United States Patent [19]

Childress et al.

[11] 4,035,262

[45] July 12, 1977

[54] ACROLEIN OXIDATION CATALYST

[75] Inventors: David L. Childress, Angleton; William V. Hayes; Richard L. Poppe, both of Clute, all of Tex.

[73] Assignee: The Dow Chemical Company, Midland, Mich.

[21] Appl. No.: 678,274

[22] Filed: Apr. 19, 1976

[51] Int. Cl.² .................. B01J 21/08; B01J 23/22; B01J 23/26; B01J 23/28
[52] U.S. Cl. .............................. 252/456; 252/464; 252/467; 260/530 N
[58] Field of Search .................. 252/456, 464, 467; 260/530 N

[56] References Cited

U.S. PATENT DOCUMENTS 3,853,792  12/1974  Ohara et al. ..................... 252/467
3,926,915  12/1975  Watanabe et al. ............ 252/456 X Primary Examiner—W. J. Shine
Attorney, Agent, or Firm—A. Cooper Ancona

[57] ABSTRACT

A method of preparing acrylic acid by oxidation of acrolein over a new and improved catalyst providing conversions of acrolein of greater than 99% with yields of acrylic acid in excess of 95%. The catalyst consists essentially of the oxides of molybdenum, vanadium, chromium and copper and at least one of tantalum and niobium and optionally silicon on an inert carrier. Catalysts useful in the process contain the elements previously mentioned in the atomic ratios of $$Mo_{15}V_{5-10}Cu_{2-5}Cr_{0.2-2}M_{0.1-3}$$

where M is tantalum, niobium or mixtures thereof.

5 Claims, No Drawings

ACROLEIN OXIDATION CATALYST

BACKGROUND OF THE INVENTION

In the process of making acrylic acid the most widely used processes are those which oxidize propylene or acrolein to acrylic acid. Many different combinations of metal oxides have been used as catalysts. Most of these contain molybdenum oxide as the principal component. Some of the catalyst are effective in oxidizing the propylene directly to acrylic acid although this is frequently a function of the conditions under which the catalyst is used; others oxidize acrolein to the acid. In either case, any acrolein not converted, or acrolein made in the process of oxidizing propylene to acrylic acid, may be recycled to the feed stream and subsequently oxidized to form the acrylic acid.

In addition to molybdenum oxide, the catalysts of the prior art contain many other metals (usually as their oxides) which promote the catalytic effect of the molybdenum. The transition metals of Group VIII of the periodic chart, including iron, cobalt and nickel, have been employed in many such catalysts. Others selected from various groups of metals of the periodic chart have been employed. Thus, for example, titanium, vanadium, chromium, tungsten and manganese in groups IVB, VB, VIB, and VIIB are known to be useful. From group IIA such metals as magnesium, calcium, strontium and barium; from groups IB and IIB copper, silver, zinc and cadmium; also from groups IA and VA sodium, potassium, antimony and bismuth; all have been taught as catalytic promotor components. Phosphorous has been employed, usually added as phosphoric acid or as metal phosphates, as an essential part of many of the prior art catalysts. Some of the early catalysts employed molybdenum oxide in combination with 1 to 2 other metals, e.g. U.S. Pat. No. 2,881,212 which employed several metals as phosphomolybdates. In more recent years, catalysts containing 3-6 or as many as 8-10 different metals have been disclosed.

The art known to the invention as being closest to that of the present invention is found in U.S. Pat. Nos. 3,775,474; 3,833,649; 3,886,092 which teach the use of Mo, V, Cr, Cu and W in various combinations. None of these teach the use of tantalum or niobium as taught by the present invention, nor does the instant catalyst composition contain the tungsten taught by the above three U.S. patents. Another U.S. Pat. No. 3,865,873 employs tantalum together with molybdenum and phosphorous, but contains none of the other components of the catalyst of this invention.

The efficiency of the catalysts made from any particular combination of metals apparently is affected by the manner in which they are made, and whether or not it is supported or in pelleted form. The porosity and the surface area of either the pellet or the support are important to the performance of the catalyst and will determine to some extent the amount of catalytic material employed on the support. It is extremely important in the preparation of the catalyst to obtain uniform distribution of the various oxides contained therein, otherwise the effect of the combination may be lost. The molybdenum and the various promoter metals are added as their soluble salts, usually in acid solution. They are sometimes mixed together in the same solution, but because of possible problems with premature recipitation which would cause non-uniformity in the finished catalyst the metals are most frequently made up in separate solutions which are in turn added together under the proper controlled conditions. Generally, the final pH of the solutions is slightly on the acid side, at about pH 6-6.5. The solvent is then evaporated from the solution of the catalyst components in the presence of a support in order to burden it, when a support is used. If not supported, the components are dried and pelleted. Most of the techniques associated with the manufacture of the catalyst are well known to the prior art. The particular techniques used to make the catalyst of the present invention will be enumerated and exemplified herein.

The parameters of feed composition, flow rate, temperature and pressure are well known to the prior art. Thus the aldehyde is usually present in the feed stream from about 1-10 volume %, the remainder being molecular oxygen (0.8 to 21 vol. %) and inert gas. Steam is frequently used as the inert gas although since air is usually employed as the source of oxygen, nitrogen is also present as an inert gas component. Temperatures employed are within the range of 200°-400°C and pressures of from about 1-10 atm. are commonly used. Contact times are usually on the order of 0.4 to about 15 seconds depending upon the temperature employed and the efficiency of the particular catalyst.

DETAILED DESCRIPTION OF THE INVENTION

The present invention is the vapor phase oxidation of acrolein to acrylic acid over a catalyst consisting essentailly of molybdenum, vanadium, chromium, copper and at least one of tantalum and niobium. Silicon may also be employed. All of these elements are present in the form of their oxides and the catalyst is preferably employed on an inert support. The operable ratio of the atoms of the above elements in the catalyst of this invention is $$Mo_{15}V_{5-10}Cu_{2-5}Cr_{0.2-2}M_{0.1-3}Si_{1-5}.$$

A more preferred catalyst is one containing atomic ratios of $$Mo_{15}V_{5-7}Cu_{2.4-2.8}Cr_{0.7-0.8}M_{1.5-2}Si_{1-3}$$

where M is tantalum, niobium or mixtures thereof, it being understood that silicon is optional in both operable and preferred catalysts.

The tantalum pentoxide which is employed as a component is insoluble and difficult to incorporate into the catalyst mixture and as a result is generally slurried in a solution of the other components. A particularly preferred method of making the solution of catalyst components is to employ the tantalum pentoxide as a colloidal suspension. The commercially available oxide powder is run through a colloid mill prior to mixing with the silica (when silica is employed) and then added to the remaining components as described in Examples 1 and 16. The use of the finely divided colloid produces a superior catalyst.

As previously mentioned, it is known in the art that the amount of catalyst used will depend, at least in part, upon the porosity and surface area of the particular inert support employed. In the present invention the total amount of catalytic oxides burdened on the support is from about 13% to about 30% by weight based on the combined weight of catalyst and support. A preferred burden is from about 18% to about 23%. The preferred support is alumina and the surface area of the preferred support should be not more than 2 m²/g with a porosity of 35–65%, 90% of the pores being in the diameter range of 50–1500 microns.

EXAMPLE 1

Preparation of Catalyst

In a representative preparation of the present invention, a first solution was prepared by heating 1400 mls of distilled water to which was added 172.7 gms of ammonium molybdate, 43.9 gms of ammonium metavanadate, and 6.0 gms of ammonium dichromate. A second solution was prepared by adding 43.9 gms of cupric nitrate to 75 mls of distilled water which had been acidified with 3 mls of concentrated nitric acid. A third solution was prepared by adding 27.5 gms of tantalum pentoxide to 28.3 mls of Ludox L.S. (a 30% colloidal solution of silica).

The second solution was added drop-wise to the first solution with stirring and heating. Upon the completion of this addition, the third solution is added to the other two with continued heat and stirring. The carrier support (Norton S.A. 5205, ¼-inch spheres of alumina) was preheated in an oven at 150° C and then added to the composite solution above with continued heating and stirring to remove the excess water. When most of the water had been removed, the carrier was placed in an oven at 150° C for 1 hour to dry it. The dried catalyst was then calcined for a period of about 6½ hours the temperature being gradually increased from about 200° to 400° C over a period of about 1½ hours. The temperature was then maintained at 400° for the remainder of the time. The finished catalyst was removed and cooled prior to use. The catalyst prepared as above contained about 19.2 wt. % of the metal oxides on the catalyst support, and the atomic ratios of the metals were were

$Mo_{15}V_{5.7}Cr_{0.73}Cu_{2.76}Ta_{1.89}Si_{2.59}$

EXAMPLE 2

Utilization of Catalyst

The catalyst of Example 1 was placed in a stainless steel reactor made of a 1-inch tube 10 feet long within a concentric pipe which contained a heat exchange fluid for temperature control. The feed to the reactor contained 5.6 mole % acrolein, 30 mole % nitrogen (as diluent) and oxygen; the oxygen to acrolein mole ratio being 1.48. Temperature in the reactor was 300° C. Contact time was 2.9 seconds. This feed stream when passed through the reactor over the above catalyst resulted in a conversion of 99% of the acrolein and gave a selectivity to acrylic acid of 93.4% with 4.4% going to carbon oxides. In like manner, catalysts of varying compositions were tested. The mole % acrolein in the feed of each of the following Examples was in the range of from about 4.5 to about 5.5%. The results are shown in Table I.

TABLE I

| Example Number | Mo | V | Cr | Cu | Ta | Nb | Si | Temp (°C) | Time (sec) | Conv. (% Acrn) | Selectivity % A A | % Carbon Oxides |
|---|---|---|---|---|---|---|---|---|---|---|---|---|
| 3 | 15 | 5.7 | 0.72 | 2.76 | 3.08 | — | 2.59 | 300 | 2.7 | 91 | 92 | 7.0 |
| 4 | 15 | 6.67 | 0.93 | 3.22 | 2.2 | — | 2.92 | 280 | 3.5 | 95 | 89 | 9.6 |
| 5 | 15 | 5.7 | 0.72 | 2.76 | 1.89 | — | — | 289 | 2.5 | 95.1 | 94.8 | 5.2 |
| 6 | 15 | 5.7 | 0.72 | 2.76 | 1.89 | — | 2.59 | 300 | 2.9 | 99.5 | 93.0 | 6.0 |
| 7 | 15 | 5.7 | 1.09 | 2.76 | 1.89 | — | — | 301 | 2.2 | 89.8 | 91.2 | 8.8 |
| 8 | 15 | 5.71 | 0.74 | 2.76 | — | 1.78 | 4.2 | 283 | 3.7 | 96.0 | 88 | 9.5 |
| 9* | 15 | 5.47 | 0.71 | 2.64 | 1.82 | — | 2.9 | 276 | 3.2 | 98 | 91 | 9.0 |
| 10 | 15 | 7.48 | 1.51 | 2.75 | — | 1.14 | — | 280 | 3.1 | 89.4 | 88.1 | 10.2 |
| 11** | 15 | 5.75 | 0.73 | 2.78 | 1.89 | — | — | 289 | 2.2 | 94.9 | 96.3 | 3.7 |

*Only 2.6 mole % acrolein was employed in the feed stream
**Catalyst was made employing a colloidal form of tantalum

COMPARATIVE EXAMPLES

In order to show that each of vanadium, chromium, copper and tantalum or niobium is necessary to assure the good performance of the catalyst of the present invention, catalyst compositions substantially identical to that of Example 5, save one of the above components, were run in the manner of Example 2. Results are shown in Table II wherein catalysts outside the scope of the present invention were employed.

TABLE II

| Example Number | Mo | V | Cr | Cu | Ta | Nb | Si | Temp. (°C) | Time (sec) | Conv. % | Selectivity % A A | % C. oxides |
|---|---|---|---|---|---|---|---|---|---|---|---|---|
| 12 | 15 | — | 0.7 | 2.78 | 1.9 | — | 2.63 | 310 | 2.7 | 4.3 | 37 | 63 |
| 13 | 15 | 5.76 | — | 2.78 | 1.9 | — | 2.59 | 310 | 2.7 | 66.8 | 86.4 | 14.5 |
| 14 | 15 | 5.75 | 0.7 | — | 1.9 | — | 2.63 | 310 | 2.7 | 31.4 | 66.7 | 33.3 |
| 15 | 15 | 5.75 | 0.7 | 2.78 | — | — | — | 301 | 2.7 | 92.8 | 83.2 | 17.2 |

As can be seen from Table II, omitting any one of vanadium, chromium copper and tantalum will give both lowered conversions and selectivities as well as high carbon losses.

EXAMPLE 16

In a preferred preparation of the catalyst of the present invention, a first solution was prepared by heating 6000 ml of distilled water to which was added 1427.6 g of ammonium molybdate, 362.8 g of ammonium metavanadate, and 49.0 g of ammonium dichromate. A second solution was prepared by adding 363 g of cupric nitrate to 150 ml of distilled water which had been acidified with 20 ml of concentrated nitric acid. A third solution was prepared by adding 226.4 g colloidal tantalum pentoxide, less than 1 micron in size, to 500 ml water.

The second solution was added drop-wise to the first solution with stirring and heating. Upon the completion of this addition, the third solution is added to the other two with continued heat and stirring. The carrier support (Norton S.A. 5205, ¼-inch spheres of alumina) was preheated in an oven at 150° C and then added to the composite solution above with continued heating and stirring to remove the excess water. When most of the water had been removed, the carrier was placed in an oven at 150° C for 1 hour to dry it. The dried catalyst was then calcined for a period of about 6½ hours the temperature being gradually increased from about 200° to 400° C over a period of about 1½ hours. The temperature was then maintained at 400° C for the remainder of the time. The finished catalyst was removed and cooled prior to use. The catalyst prepared as above contained about 22.3% wt. % of the metal oxides on the catalyst support, and the atomic ratios of the metals were $Mo_{15}V_{5.75}Cr_{0.73}Cu_{2.78}Ta_{1.9}.$ The above catalyst, when employed to oxidize acrolein in the manner of Example 2, gave a 99.8% conversion of acrolein and a selectivity of 96.5% to acrylic acid.

EXAMPLE 17

A catalyst for the oxidation of propylene to acrolein, disclosed by the present inventors in an application filed in the U.S. Patent and Trademark Office Dec. 15, 1975, (Ser. No. 640,616), was employed in conjunction with a catalyst of the present invention in sequential operation in the following manner:

A metal oxide composition containing atomic metal ratios of $Mo_{15}Co_{6.7}Fe_{1.35}Bi_{1.3}K_{.011}$ formed into pellets ¼-inch diameter and ¼-inch thick was placed into a first column, stainless steel tubular reactor 12 ft tall and 1¼-inch diameter. A conduit connected this first column with a second column 19 ft long × 1½-inch I.D. of the same stainless steel into which was packed the supported catalyst of Example 16. Each column was heated by means of a heat exchange fluid flowing through an outer concentric tube. To the first column was fed a gas stream containing 5.3 mole percent propylene, 9.4 mole percent oxygen, and balance nitrogen at a pressure of 28.7 psig and a flow rate of 12.5 lb/hr to obtain a contact time of 2.19 seconds. The feed was preheated to a temperature of 325° C and the first reaction column was maintained at 331° C. The exit stream was passed through the conduit to the second column which was maintained at 279° C. Contact time in the second column was 4.87 seconds. The exit gases from the second column were quenched and the noncondensible gases were recycled to the first column. Conversion of propylene was 98.3% and yield to acrylic acid was 89%.

Each of the catalysts employed in the preceeding 17 examples was adhered to a spherical alumina support of about ¼-inch diameter. In Table III the support employed for each catalyst and the loading (weight % catalyst employed based on total weight of catalyst and support) is given. Supports A, B and C had different porosities and surface areas as follows:

A = 49–55% porosity; 90% of the pores in 50–1500 micron range; 0.005–0.5 m²/g surface area.

B = 60.2% porosity; 90% of the pores in 50–1500 micron range; 0.024 m²/g surface area.

C = 38–42% porosity; 90% of the pores in 50–1500 micron range; 0.005–0.04 m²/g surface area.

TABLE III

| Example Number | Carrier | Loading (wt. %) |
| --- | --- | --- |
| 1 | A | 19.2 |
| 2 | A | 19.2 |
| 3 | B | 19.8 |
| 4 | C | 18.6 |
| 5 | A | 21.6 |
| 6 | A | 24.0 |
| 7 | A | 24.6 |
| 8 | C | 13.1 |
| 9 | C | 21.7 |
| 10 | A | 26.4 |
| 11 | A | 24.3 |
| 12 | A | 23.7 |
| 13 | A | 24.0 |
| 14 | A | 24.3 |
| 15 | A | 23.9 |
| 16 | A | 22.3 |
| 17 | A | 22.3 |

We claim:

1. A supported catalyst suitable for oxidizing acrolein to acrylic acid which contains oxides of molybdenum, vanadium, chromium, copper and at least one of an oxide of tantalum and niobium on an inert support, wherein the atomic ratios of the metals are $Mo_{15}V_{5-10}Cr_{0.2-2}Cu_{2-5}M_{0.1-3}$ wherein M is tantalum, niobium or mixtures thereof.

2. The catalyst of claim 1 which additionally contains silicon as its oxide in the ratio of 1–5 atoms of silicon.

3. The catalyst of claim 1 wherein the atomic ratios of the metals are $Mo_{15}V_{5-7}Cr_{0.7-0.8}Cu_{2.4-2.8}M_{1.5-2}$ 4. The catalyst of claim 3 which additionally contains silicon as its oxide in the ratio of 1–3 atoms of silicon.

5. The catalyst of claim 3 wherein the support is alumina having a surface area of not more than 2 m²/g and a porosity of 35–65%, 90% of the pores being in the range of 50–1500 microns in diameter.

* * * * *